United States Patent [19]

Beck, Jr. et al.

[11] Patent Number: 5,339,809

[45] Date of Patent: Aug. 23, 1994

[54] METHOD OF INSERTING A CRICOTHYROIDAL ENDOTRACHEAL DEVICE BETWEEN THE CRICOID AND THYROID CARTILAGES FOR TREATMENT OF CHRONIC RESPIRATORY DISORDERS

[76] Inventors: Charles A. Beck, Jr., 2922 Imperial Ct.; Natan Scher, 2923 Mack Heath Crescent, both of Flossmoor, Ill. 60422

[21] Appl. No.: 59,187

[22] Filed: May 6, 1993

Related U.S. Application Data

[63] Continuation of Ser. No. 802,355, Dec. 4, 1991, abandoned.

[51] Int. Cl.⁵ .................. A61M 5/178; A61M 25/00; A61M 16/00
[52] U.S. Cl. .................. 128/207.29; 128/207.15; 128/911; 604/165; 604/280
[58] Field of Search .................. 128/207.14, 207.15, 128/207.29, 200.26, 911, 912; 604/96, 116, 165, 280

[56] References Cited

U.S. PATENT DOCUMENTS

| | | | |
|---|---|---|---|
| 3,087,493 | 4/1963 | Schossow | 128/207.15 |
| 3,599,642 | 8/1971 | Jindel | 128/207.14 |
| 3,682,166 | 8/1972 | Jacobs | 128/207.14 |
| 3,688,773 | 9/1972 | Weiss | 128/207.29 |
| 3,794,026 | 2/1974 | Jacobs | 128/207.15 |
| 3,799,173 | 3/1974 | Kamen | 128/207.15 |
| 4,026,296 | 5/1977 | Stoy et al. | 128/207.15 |
| 4,269,184 | 5/1981 | Montgomery | 128/207.14 |
| 4,471,776 | 9/1984 | Cox | 128/207.15 |
| 4,488,545 | 12/1984 | Shen | 128/207.29 |
| 4,716,901 | 1/1988 | Jackson et al. | 128/200.26 |
| 4,987,895 | 1/1991 | Heimlick | 128/207.14 |
| 5,090,408 | 2/1992 | Spofford et al. | 128/207.14 |

*Primary Examiner*—Kimberly L. Asher
*Attorney, Agent, or Firm*—Rudnick & Wolfe

[57] ABSTRACT

A method for providing continuous oxygen therapy to a patient having chronic breathing problems wherein the method includes the steps of providing cricothyroidal-endotracheal device and having a hollow tube of semi-rigid material having a plurality of spaced holes extending through the tube wall and connected at its proximal end to the distal end of a flexible hollow tube, in turn, connected at its proximal end to the distal end of a hollow semi-rigid tube for connection to an oxygen supply source for feeding oxygen through such connected tubes and the holes through the semi-rigid tube wall and a flange fixed to the outer wall of the oxygen supply tube, providing an oxygen source, creating a surgical opening in the patient, inserting the device through the surgical opening, positioning the device in the surgical opening and the trachea, connecting the device to the oxygen supply, delivering oxygen through the device, and leaving the device in the place in the surgical opening for extended period of time to treat the patient. In a further embodiment of the invention, the tubing can have a pleated section and an inflatable collar to assist in positioning the tubing within the trachea.

5 Claims, 2 Drawing Sheets

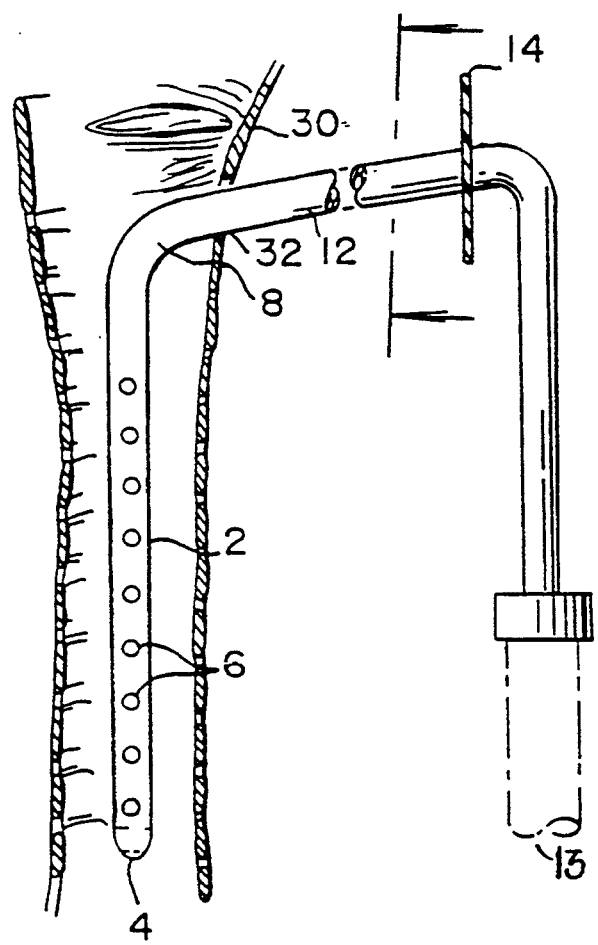

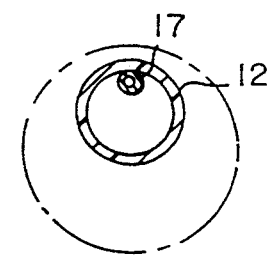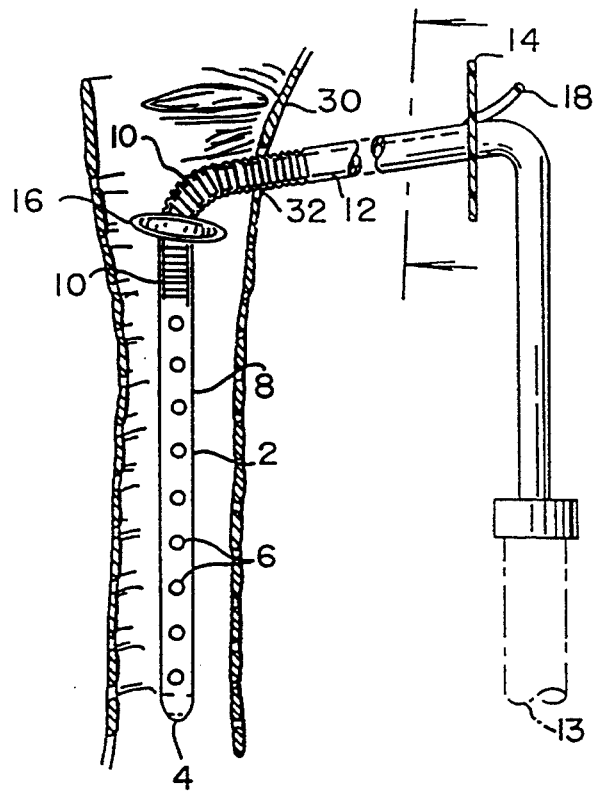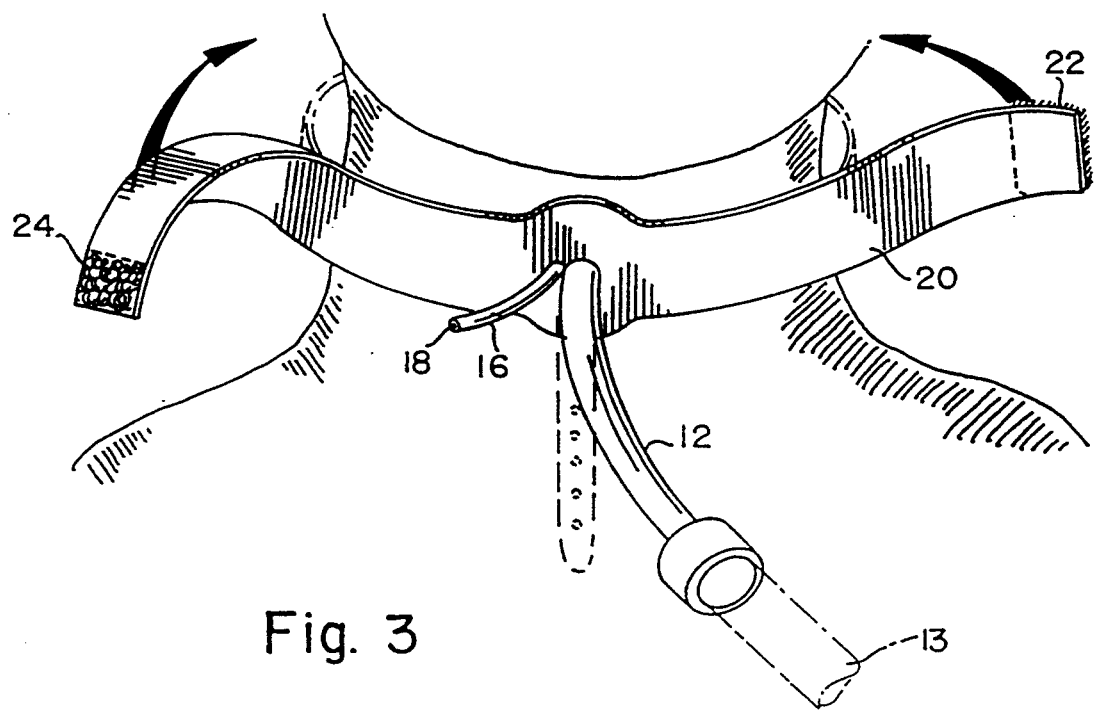

METHOD OF INSERTING A CRICOTHYROIDAL ENDOTRACHEAL DEVICE BETWEEN THE CRICOID AND THYROID CARTILAGES FOR TREATMENT OF CHRONIC RESPIRATORY DISORDERS

This application is a continuation, of application Ser. No. 07/802,355, filed Dec. 4, 1991, now abandoned.

This invention relates to apparatus for administering oxygen to patients having serious breathing problems and, more particularly, to patients requiring air oxygen enrichment for breathing.

The most commonly used prior art procedure and apparatus for use with patients having chronic breathing problems requiring air oxygen enrichment is a tracheostomy in which a rather substantially sized hole is made through the second, third or fourth ring of tracheal cartilage in a patient's neck below the voice box through which a relatively large diameter tube is inserted into the patient's trachea, with the tube end, in the trachea, extending downward toward the lungs. Such tracheostomy has a number of disadvantages. The large hole made through the tracheal cartilage may become permanent. Because the hole is large and is at a distance below the patient's voicebox, the patient cannot talk with a normal voice unless special measures are undertaken. The tracheostomy tube is subject to plugging with secretions and there is leakage of air around the edge of the tubing. The tube tends to irritate the patient and the patient's throat and cause coughing. The patients are forbidden to take showers unless the tracheostomy tube has been plugged.

Another procedure used with patients, especially where emergency procedure is required which can be completed in one or two minutes to relieve an airway obstruction is a cricothyrotomy. In this procedure usually a large hole, as in a tracheostomy, but higher in the neck, between the cricoid cartilage and the thyroid cartilage, is made. This procedure is used only for short term solution of an emergency. The doctor must enter the neck substantially perpendicular to the skin, the tube, as used in a tracheostomy, is pushed inwardly and downwardly between the cricoid and thyroid cartilages and then downward in the tracheal cavity. Care must be exercised so as to not injure the cartilage and such procedure can result in infection and necrosis of the cricoid. The patient cannot speak while the tube is in place. Typically, the tubing is removed within a week and replaced by a tracheostomy, lower in the trachea, to avoid infection and destruction of the voice box, or larynx, skeleton that may result in severe subglottic stenosis and the loss of the ability to speak or breathe through the voice box.

In the present invention, a procedure and an apparatus for carrying out such procedure is provided wherein tracheal oxygen is administered to patients with chronic breathing problems using novel tubing and a modified cricothyrotomy procedure not normally used with chronic patients. Unlike tracheostomy and emergency cricothyrotomy where relative large diameter tubes, requiring relative large openings, are employed, in the instant invention a relatively small diameter tube having a semi-rigid distal end with a plurality of perforations or holes therealong for oxygen passage from the tube interior to the tube exterior, an accordion pleated tube section or a constant 90°-130° angled portion connected at its distal end to the proximal end of the semi-rigid perforated tube and having substantially the same effective diameter as such semi-rigid tube and a further tube of substantially the same diameter as the semi-rigid tube is connected at its distal end to the proximal end of the accordion semi-rigid tube or constant angled portion for connection at its proximal end to an oxygen or oxygen enriched air source.

The invention of the present application will be more fully understood from the following description taken with the appended drawings in which FIG. 1 is a side view, partly in section, showing the device of one embodiment of the present invention, in place and extending into the trachea;

FIG. 2 is a side view, partly in section, showing another embodiment of the present invention, in place and extending into the trachea.

FIG. 3 is a view, similar to FIG. 1 but taken from the front; and

FIG. 4 is a sectional view taken at 3—3, FIG. 1.

Referring to FIG. 1, the tube for administering endotracheal oxygen in accordance with the instant invention comprises an end tube section 2 of semi-rigid material, closed or open at its distal end 4 and having holes 6 therealong, regularly or randomly spaced, and having a substantially semi-rigid cylindrical configuration. Tube section 2 is joined, at its proximal end, to the distal end of a tube 8 of substantially the same diameter as tube section 2. As shown, an angle of 90° to 130° is provided between ends of tube 8. Tube 8 is connected to a tube 12. The distal end of tube 8 is connected to an oxygen or oxygen enriched air source 13. A flange 14 is fixed to tube 12 for purposes described hereinafter.

A second embodiment of a tube for administering endotracheal oxygen is illustrated in FIG. 2. The second embodiment of the tube has a similar structure to that of the first embodiment illustrated in FIG. 1 and similar structural elements between the two tubes are indicated by identical reference members. In the second embodiment of the tube, the tube section 8 is configured with accordion pleats 10 between opposite ends thereof to form a flexible connection between the proximal end of tube 2 and the distal end of tube 12. Moreover, this second embodiment of the tube is preferably provided with a balloon or cuff 16 fixed to the flexible tube 8. The cuff is conventionally inflated and deflated through a conventional air passageway 17 (FIG. 3) formed in the wall of tubes 8 and 12 or by a small tube extending along inner or outer walls of tube 8 and 12. A distal end of passageway 17 is formed with a port 18 for inflation and deflation of the balloon or cuff 16, for purposes later described.

Either embodiment of the tube assembly may be formed with or passed through a suitable sized opening in a collar 20 (FIG. 4), collar 29 is preferably formed of soft silicone, or other soft material suitable for use as a collar, and provide, at its ends, with hook and loop fastening material such as sold under the Trademark VELCRO 22, 24 or with other suitable means for attachment to the patient.

For reasons more apparent later herein, flexibility of tube sections 2 and 8, flexibility of tube section 8 being, of course, enhanced by accordion pleats 10, or other means, is of importance to the insertion and removal of the apparatus of the instant invention. A tube having an outer diameter of between about 5 mm and about 9 mm and an inner diameter of between about 3 mm and about 5 mm and of a material, such as, silicon tubing, is preferred. Tubing of a material, such as used in nasal gastric tubing has been found suitable.

In the use of the novel tube of the instant invention, a small hole of sufficient size to receive the end tube section 2, pleated tube section 8, and the distal end of tube 12 is made in the front face of the patient's upper neck through the skin, flesh and membrane between upper margin of the cricoid cartilage 32, FIG. 1, and the lower margin of the thyroid cartilage 30 and into the trachea.

The end 4 of tube 2 of semi-rigid material is inserted through the hole into the trachea and in a downward direction, the end 4 of tube 2 sliding along the rear surface of the trachea until tube section 8, having accordion pleats 10, or the constant angled portion, enters the trachea. Because of the flexibility of tube section 8, when properly inserted, tube 2 hangs, free, in the trachea. Flange 14 on tube 12, which may be a disc on the exterior of tube 12 or a part of collar 20, if such collar is used, prevents the tube from being inserted to deeply into the trachea. Thus, the end 4 of the tube is just above the bifurcation of the trachea into the right and left bronchae.

With the tubes 2 and 8 inserted, balloon, or cuff 16 is inflated thereby preventing the tube from being withdrawn while the balloon or cuff 16 is inflated and positions the tube substantially in the center of the trachea. The proximal or free end of tube 12 is connected to an oxygen or oxygen enriched air source and oxygen or oxygen enriched air is administered to the patient and adjusted to the required flow.

Tubes 2 and 8 are relatively small and narrow, especially as compared to tubes used in tracheostomies, do not disrupt normal ventilation mechanics in the airway, avoid the problems of coughing and irritation normally experienced with tracheostomiea patients, and have sufficient flexibility that, when in place in the trachea, move out of the way when the patient moves his head, swallows or breathes naturally. Patients can take showers without the risk of "drowning". When properly inserted, there is minimal or no air leakage and, with a portable oxygen or oxygen enriched air, is especially suited for ambulatory patients.

The terms and expressions which have been employed in the foregoing description are used as terms of description and not of limitation, and there is no intention, in the use of such terms and expressions, of excluding any equivalents of the features shown and described or portions thereof, but it is recognize that various modifications are possible within the scope of the invention claimed.

What is claimed

1. A method for providing continuous oxygen therapy to a patient having chronic breathing problems, said method comprising the steps of:
   A) providing a cricothyroidal endotracheal apparatus including:
      a first elongated and hollow tube portion formed of semi-rigid material and having an outer diameter between approximately 5 and 9 mm, and substantially less than the inside diameter of the trachea, means to prevent damage to the trachea during insertion comprising a closed distal end which tapers downwardly towards said distal end, a plurality of vertically spaced apertures extending away from said distal end, said vertically spaced apertures allowing fluid to flow between an interior and an exterior of said first tube portion;
      a second hollow and elongated tube portion having an outer diameter between approximately 5 and 9 mm and substantially less than the inside diameter of the trachea to prevent damage to the trachea during insertion of said second hollow and elongated tube portion, said second hollow and elongated tube portion having a proximal end, a distal end, and an intermediate portion, said intermediate portion of said second hollow and elongated tube portion having a structure permitting angular displacement between an angle of 90 and 130 degrees;
      a third hollow tube portion including a flange for maintaining at least a proximal end of said third hollow tube portion outside of a patient, and a distal end having an outer diameter between approximately 5 and 9 mm;
   B) providing an oxygen source;
   C) connecting said proximal end of said first hollow elongated tube portion to the distal end of said second hollow elongated tube portion, and the proximal end of said second hollow elongated tube portion to the distal end of said third hollow tube portion;
   D) creating a surgical opening between an upper margin of the cricoid cartilage and a lower margin of the thyroid cartilage sized according to the outer diameter of said first, second, and third hollow tube portions, between approximately 5 and 9 mm;
   E) in a single step, without the use of a needle-mounted catheters and intermediate dilators, inserting said closed distal end of said first hollow and elongated tube portion, and the distal and intermediate portion of said second hollow and elongated tube portion through said surgical opening;
   F) positioning said first hollow and elongated tube portion at an angle of 90 to 130 degrees to said surgical opening by angularly displacing said intermediate portion of said second hollow and elongated tube portion, and thereby:
      preventing said closed distal end of said first hollow and elongated tube portion from touching the tracheal walls;
      maintaining said first hollow and elongated tube portion such that it hangs freely in the trachea; and
      substantially eliminating disruption of normal ventilation of the patient by allowing flow around said cricothyroidal endotracheal apparatus;
   G) connecting said proximal end of said third hollow tube portion to said oxygen supply;
   H) delivering a low pressure oxygen flow through said cricothyroidal endotracheal apparatus through said third hollow tube portion, said second hollow tube portion, said first hollow tube portion and said vertically spaced apertures to the trachea of the patient at a flow rate promoting oxygen enrichment at the closed distal end of said third hollow tube portion; and
   I) leaving said cricothyroidal endotracheal apparatus in place in said surgical opening for an extended period of time for treatment of the chronic patient.

2. The method for providing continuous oxygen therapy according to claim 1 further including the step of:
   configuring said tube portions extending between the distal end of the apparatus and the flange with an inner diameter ranging between about 3 mm to about 5 mm.

3. The method for providing continuous oxygen therapy according to claim 2 further including the step of:

forming at least said first and second hollow tube portions from a material from the class including flexible plastic to allow the apparatus to adapt to the patient's trachea when the trachea moves.

4. The method for providing continuous oxygen therapy in a patient according to claim 1 including the further step of:

using a collar for inhibiting movement of the flange of the apparatus relative to the patient, said collar having flexible arms which engage and extend outwardly from the flange for extension around the neck of the patient and have connectors toward their distal ends for releasably securing the ends to each other whereby maintaining the flange in place relative to the patient's neck.

5. A method for providing continuous oxygen therapy to a patient having chronic breathing problems, said method comprising the steps of:

A) providing a cricothyroidal endotracheal apparatus including;

a first elongated and hollow tube portion formed of semi-rigid material and having an outer diameter between approximately 5 and 9 mm, and substantially less than the inside diameter of the trachea, means to prevent damage to the trachea during insertion comprising a closed distal end which tapers downwardly towards said distal end, a plurality of vertically spaced apertures extending away from said distal end, said vertically spaced apertures allowing fluid to flow between an interior and an exterior of said first tube portion;

a second hollow and elongated tube portion having an outer diameter between approximately 5 and 9 mm and substantially less than the inside diameter of the trachea to prevent damage to the trachea during insertion of said second hollow and elongated tube portion, said second hollow and elongated tube portion having a proximal end, a distal end, and an intermediate portion, said intermediate portion of said second hollow and elongated tube portion having a pleating structure permitting angular displacement between an angle of 90 and 130 degrees;

a third hollow tube portion including a flange for endwise positioning the apparatus and for maintaining at least a proximal end of said third hollow tube portion outside of a patient, and a distal end having an outer diameter between approximately 5 and 9 mm;

B) providing an oxygen source;

C) connecting said proximal end of said first hollow elongated tube portion to the distal end of said second hollow elongated tube portion, and the proximal end of said second hollow elongated tube portion to the distal end of said third hollow tube portion;

D) creating a surgical opening between an upper margin of the cricoid cartilage and a lower margin of the thyroid cartilage sized according to the outer diameter of said first, second, and third hollow tube portions, between approximately 5 and 9 mm;

E) in a single step, without the use of a needle-mounted catheters and intermediate dilators, inserting said closed distal end of said first hollow and elongated tube portion, and the distal and intermediate portion of said second hollow and elongated tube portion through said surgical opening;

F) inflating a nonoccluding cuff circumferentially arranged about a section of said second tube portion proximate to said surgical opening following insertion of said apparatus through the opening to inhibit endwise movement of said apparatus relative to said surgical opening;

G) positioning said first hollow and elongated tube portion at an angle of 90 to 130 degrees to said surgical opening by angularly displacing said intermediate portion of said second hollow and elongated tube portion, and thereby:

preventing said closed distal end of said first hollow and elongated tube portion from touching the tracheal walls;

maintaining said first hollow and elongated tube portion such that it hangs freely in the trachea; and substantially eliminating disruption of normal ventilation of the patient by allowing flow around said cricothyroidal endotracheal apparatus;

H) connecting said proximal end of said third hollow tube portion to said oxygen supply;

I) delivering a low pressure oxygen flow through said cricothyroidal endotracheal apparatus through said third hollow tube portion, said second hollow tube portion, said first hollow tube portion and said vertically spaced apertures to the trachea of the patient at a flow rate promoting oxygen enrichment at the closed distal end of said third hollow tube portion; and J) leaving said cricothyroidal endotracheal apparatus in place in said surgical opening for an extended period of time for treatment of the chronic patient.

* * * * *